(12) United States Patent
Voegele et al.

(10) Patent No.: US 8,457,718 B2
(45) Date of Patent: Jun. 4, 2013

(54) RECOGNIZING A REAL WORLD FIDUCIAL IN A PATIENT IMAGE DATA

(75) Inventors: James W. Voegele, Cincinnati, OH (US); Robert M. Trusty, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1045 days.

(21) Appl. No.: 11/726,257

(22) Filed: Mar. 21, 2007

(65) Prior Publication Data
US 2008/0234566 A1    Sep. 25, 2008

(51) Int. Cl.
*A61B 5/05* (2006.01)

(52) U.S. Cl.
USPC .............................................. 600/426

(58) Field of Classification Search
USPC .............................................. 600/426
See application file for complete search history.

(56) References Cited

U.S. PATENT DOCUMENTS

| | | |
|---|---|---|
| 5,391,199 A | 2/1995 | Ben-Haim |
| 5,398,691 A | 3/1995 | Martin et al. |
| 5,497,934 A | 3/1996 | Brady et al. |
| 5,575,288 A | 11/1996 | Sliwa, Jr. et al. |
| 5,636,255 A | 6/1997 | Ellis |
| 5,728,044 A | 3/1998 | Shan |
| 5,729,129 A * | 3/1998 | Acker ................... 324/207.12 |
| 5,771,896 A | 6/1998 | Sliwa, Jr. et al. |
| 5,772,594 A | 6/1998 | Barrick |
| 5,836,869 A | 11/1998 | Kudo et al. |
| 5,868,673 A | 2/1999 | Vesely |
| 6,016,439 A | 1/2000 | Acker |
| 6,092,526 A | 7/2000 | LaFontaine et al. |
| 6,167,292 A | 12/2000 | Badano et al. |
| 6,252,599 B1 | 6/2001 | Natsuko et al. |
| 6,321,106 B1 | 11/2001 | Lemelson |
| 6,381,485 B1 * | 4/2002 | Hunter et al. ................ 600/407 |
| 6,428,547 B1 | 8/2002 | Vilsmeier |
| 6,456,735 B1 | 9/2002 | Sato et al. |

(Continued)

FOREIGN PATENT DOCUMENTS

| | | |
|---|---|---|
| DE | 102005022901 | 11/2006 |
| EP | 0920838 | 6/1999 |

(Continued)

OTHER PUBLICATIONS

Invitrogen—Qdot In Vivo Imaging, 2006 Introgen Corporation, 5 pages, webpage.

(Continued)

*Primary Examiner* — Tse Chen
*Assistant Examiner* — Hien Nguyen

(57) ABSTRACT

Medical apparatus is described including a fiducial component and a position sensor. The component is recognizable as at least a part of a fiducial when appearing in image data of a patient. The component is attachable to the patient. The sensor is attachable to the component at a predetermined location and orientation on the component or is capable of being positioned adjacent the fiducial component without attachment thereto at a predetermined location and orientation. A storage medium is described containing a program which instructs the computer to recognize a predetermined shape of each of at least one portion of a position sensor as at least a part of a real-world fiducial in image data of a patient. The position sensor is adapted to provide position data. Medical apparatus which includes the position sensor and the storage medium is also described.

16 Claims, 6 Drawing Sheets

U.S. PATENT DOCUMENTS

| | | | |
|---|---|---|---|
| 6,491,702 | B2 | 12/2002 | Heilbrun et al. |
| 6,546,279 | B1 | 4/2003 | Bova et al. |
| 6,556,695 | B1 | 4/2003 | Packer et al. |
| 6,565,532 | B1* | 5/2003 | Yuzhakov et al. ............ 604/142 |
| 6,615,063 | B1 | 9/2003 | Ntziachristos et al. |
| 6,690,964 | B2 | 2/2004 | Bieger et al. |
| 6,773,402 | B2 | 8/2004 | Govari et al. |
| 7,366,562 | B2 | 4/2008 | Dukesherer et al. |
| 7,697,972 | B2 | 4/2010 | Verard et al. |
| 7,764,985 | B2 | 7/2010 | McCombs et al. |
| 7,840,256 | B2 | 11/2010 | Lakin et al. |
| 2001/0029333 | A1 | 10/2001 | Shahidi |
| 2001/0044578 | A1* | 11/2001 | Ben-Haim et al. ............ 600/424 |
| 2002/0007108 | A1 | 1/2002 | Chen et al. |
| 2002/0087101 | A1* | 7/2002 | Barrick et al. ................ 600/587 |
| 2002/0156363 | A1* | 10/2002 | Hunter et al. ................ 600/410 |
| 2003/0065294 | A1* | 4/2003 | Pickup et al. ................ 604/304 |
| 2003/0139668 | A1 | 7/2003 | Ben-Haim et al. |
| 2003/0160721 | A1 | 8/2003 | Gilboa et al. |
| 2004/0101822 | A1 | 5/2004 | Wiesner et al. |
| 2004/0105979 | A1 | 6/2004 | Bayless |
| 2004/0167391 | A1 | 8/2004 | Solar et al. |
| 2005/0020878 | A1 | 1/2005 | Ohnishi et al. |
| 2005/0020918 | A1 | 1/2005 | Wilk et al. |
| 2005/0033164 | A1 | 2/2005 | Yatsuo et al. |
| 2005/0080333 | A1 | 4/2005 | Piron et al. |
| 2005/0085793 | A1 | 4/2005 | Glossop |
| 2005/0119639 | A1* | 6/2005 | McCombs et al. ................ 606/1 |
| 2005/0152836 | A1 | 7/2005 | Ashley et al. |
| 2005/0182295 | A1 | 8/2005 | Soper et al. |
| 2005/0196028 | A1 | 9/2005 | Kleen et al. |
| 2005/0203420 | A1 | 9/2005 | Kleen et al. |
| 2006/0052701 | A1 | 3/2006 | Carter et al. |
| 2006/0058644 | A1 | 3/2006 | Hoppe et al. |
| 2006/0064006 | A1 | 3/2006 | Strommer et al. |
| 2006/0089624 | A1 | 4/2006 | Voegele et al. |
| 2006/0089625 | A1 | 4/2006 | Voegele et al. |
| 2006/0089626 | A1 | 4/2006 | Voegele et al. |
| 2006/0142657 | A1 | 6/2006 | Quaid et al. |
| 2006/0149134 | A1 | 7/2006 | Soper et al. |
| 2006/0173299 | A1 | 8/2006 | Romley et al. |
| 2006/0183246 | A1 | 8/2006 | Wiesner et al. |
| 2006/0239544 | A1 | 10/2006 | Yankelevitz et al. |
| 2006/0245971 | A1 | 11/2006 | Burns et al. |
| 2006/0271056 | A1 | 11/2006 | Terrill-Grisoni et al. |
| 2007/0147705 | A1 | 6/2007 | Clune et al. |
| 2007/0173689 | A1 | 7/2007 | Ozaki et al. |
| 2007/0191707 | A1 | 8/2007 | Denittis |
| 2007/0270685 | A1 | 11/2007 | Kang et al. |
| 2008/0086051 | A1 | 4/2008 | Voegele |
| 2008/0118103 | A1 | 5/2008 | Pescatore et al. |
| 2008/0221434 | A1 | 9/2008 | Voegele |
| 2008/0232656 | A1 | 9/2008 | Voegele |
| 2008/0234544 | A1 | 9/2008 | Voegele |
| 2008/0234720 | A1 | 9/2008 | Chang et al. |
| 2008/0298655 | A1 | 12/2008 | Edwards |
| 2008/0319307 | A1 | 12/2008 | Voegele et al. |
| 2009/0054761 | A1 | 2/2009 | Voegele et al. |
| 2009/0161927 | A1 | 6/2009 | Mori et al. |

FOREIGN PATENT DOCUMENTS

| | | |
|---|---|---|
| EP | 1410758 | 4/2004 |
| EP | 1652470 | 5/2006 |
| FR | 2779339 | 12/1999 |

OTHER PUBLICATIONS

Kodak—Kodak X-Sight Imaging Agent for In Vivo Applications, 2007, 3 pages, Webpage.

Hybrid Silica Technologies, Inc.—01. Hybrid Silica Technologies, Inc. (HST) Founded to Commercialize CU Dots Fluorescent Nanoparticles, 2004, by the Office of the Vice Provost for Research, Cornell University, 2 pages, Webpage.

U.S. Appl. No. 11/524,216, Voegele, James W., Entire.

Website document of Mimics Software from Materialise (8 pages).

PCT, International Search Report, PCT/US08/57323 (Aug. 7, 2008).

PCT, International Search Report, PCT/US08/57322 (Aug. 18, 2008).

PCT, International Search Report, PCT/US08/56043 (Aug. 26, 2008).

Supplementary Partial European Search Report, European Patent Application No. 07842741 (8 pages) (Aug. 6, 2009).

International Search Report, International Application No. PCT/US2008/054933 (3 pages) (mailed Aug. 20, 2008; published Nov. 27, 2008).

International Search Report, International Application No. PCT/US2007/078832 (2 pages) (mailed Apr. 10, 2008; published Jul. 3, 2008).

Viergever, M.A. et al., "Integration of functional and anatomical brain images," *Biophy. Chem.*, vol. 68, pp. 207-219 (1997).

Supplementary Partial European Search Report, European Application No. 07842741.6 (8 pages) (Aug. 6, 2009).

EP, Supplementary European Search Report, European Application No. 08743996.4 (Apr. 8, 2011).

EP, Decision to Grant, European Application No. 08730689.0 (Apr. 21, 2011).

PCT, International Preliminary Report on Patentability, International Application No. PCT/US2008/056043 (Sep. 15, 2009).

PCT, International Preliminary Report on Patentability, International Application No. PCT/US2008/054933 (Sep. 8, 2009).

PCT, International Preliminary Report on Patentability, International Application No. PCT/US2007/078832 (Mar. 24, 2009).

PCT, International Preliminary Report on Patentability, International Application No. PCT/US2008/057323 (Sep. 22, 2009).

PCT, International Preliminary Report on Patentability, International Application No. PCT/US2008/057322 (Sep. 22, 2009).

US, Office Action, U.S. Appl. No. 11/725,834 (Mar. 22, 2011).

US, Office Action, U.S. Appl. No. 11/726,653 (Feb. 18, 2011).

US, Office Action, U.S. Appl. No. 11/820,354 (Jun. 29, 2011).

US, Office Action, U.S. Appl. No. 11/894,841 (Feb. 25, 2011).

EP, Supplementary European Search Report, European Application No. 08730689.0; 6 pages (Apr. 28, 2010).

PCT, International Preliminary Report on Patentability, International Application No. PCT/US2008/056043; 5 pages (Sep. 15, 2009).

PCT, International Preliminary Report on Patentability, International Application No. PCT/US2008/057323; 5 pages (Sep. 22, 2009).

PCT, International Preliminary Report on Patentability, International Application No. PCT/US2008/057322; 5 pages (Sep. 22, 2009).

PCT, International Preliminary Report on Patentability, International Application No. PCT/US2007/078832; 6 pages (Mar. 24, 2009).

PCT, International Preliminary Report on Patentability, International Application No. PCT/US2008/054933; 6 pages (Sep. 8, 2009).

US, Office Action, U.S. Appl. No. 11/716,465; 15 pages (Jun. 24, 2009).

US, Office Action, U.S. Appl. No. 11/716,465; 11 pages (Mar. 16, 2010).

US, Office Action, U.S. Appl. No. 11/726,653; 22 pages (May 28, 2010).

US, Office Action, U.S. Appl. No. 11/524,216; 21 pages (Aug. 19, 2008).

US, Office Action, U.S. Appl. No. 11/524,216; 20 pages (Jan. 22, 2009).

US, Advisory Action, U.S. Appl. No. 11/524,216; 3 pages (Apr. 15, 2009).

US, Office Action, U.S. Appl. No. 11/524,216; 19 pages (Jun. 23, 2009).

US, Office Action, U.S. Appl. No. 11/524,216; 16 pages (Mar. 3, 2010).

US, Advisory Action, U.S. Appl. No. 11/524,216; 3 pages (May 11, 2010).

US, Office Action, U.S. Appl. No. 11/726,653 (Nov. 4, 2010).

US, Notice of Allowance, U.S. Appl. No. 11/726,653 (Aug. 17, 2011).

US, Office Action, U.S. Appl. No. 11/894,841 (Sep. 26, 2011).

CN, Notification of First Office Action, Chinese Application No. 200780034771.0 (Aug. 11, 2010).

CN, Notification of First Office Action, Chinese Application No. 200880012795.0 (Oct. 20, 2010).

EP, Office Action, European Application No. 07842741.6 (Oct. 12, 2010).

EP, Search Report, European Application No. 08743996.4 (Apr. 8, 2011).

US, Office Action, U.S. Appl. No. 11/894,841 (Nov. 3, 2010).

US, Office Action, U.S. Appl. No. 11/725,834 (Aug. 1, 2011).

* cited by examiner

US 8,457,718 B2

RECOGNIZING A REAL WORLD FIDUCIAL IN A PATIENT IMAGE DATA

FIELD OF THE INVENTION

The present invention is related generally to medical images, and more particularly to medical apparatus and to a storage medium containing a computer program all relating to recognizing a real world fiducial in image data of a patient.

BACKGROUND OF THE INVENTION

Imagers are known for obtaining image data of a patient and for displaying images of the image data on a display monitor. Such images include, without limitation, ultrasound images, X-ray images, computerized tomography (CT) images, positive electron emission (PET) images, magnetic resonance (MRI) images, fluoroscope images, etc. Where needed, it is known to register these images with a real world object by placing a fiducial component on the skin of the patient, wherein the fiducial component has a predetermined shape, and wherein the fiducial component is recognizable as a fiducial in the image data using pattern recognition software (e.g., a conventional segmentation subroutine).

Position sensors are known which are placed on medical instruments which are inserted into a patient allowing the position of the medical instrument to be tracked inside the patient. Such position sensors are part of known position sensing systems such as an AC-based system available from Biosense-Webster or a DC-based system available from Ascension Technology Corporation.

Still, scientists and engineers continue to seek improvements in recognizing a real world fiducial in patient image data.

SUMMARY

A first expression of a first embodiment of the invention is for medical apparatus including a fiducial component and a position sensor. The fiducial component is recognizable as at least a part of a fiducial when appearing in image data of a patient. The fiducial component is attachable to the patient. The position sensor is adapted to provide position data. The position sensor is attachable to the fiducial component at a predetermined location on the fiducial component and with a predetermined orientation with respect to the fiducial component.

A first expression of a second embodiment of the invention is for medical apparatus including a fiducial component and a position sensor. The fiducial component is recognizable as at least a part of a fiducial when appearing in image data of the patient. The fiducial component is attachable to the patient. The position sensor is adapted to provide position data. The position sensor is positionable (i.e., capable of being positioned) adjacent the fiducial component without attachment thereto at a predetermined location on the fiducial component and with a predetermined orientation with respect to the fiducial component.

A first expression of a third embodiment of the invention is for a storage medium containing a program readable by a digital computer which instructs the digital computer to recognize a predetermined shape of each of at least one portion of a position sensor as at least a part of a real-world fiducial in image data of a patient when the image data includes the predetermined shape and is received as an input by the digital computer. The position sensor is adapted to provide position data.

A second expression of a third embodiment of the invention is for medical apparatus comprising a position sensor and a storage medium. The position sensor has at least one portion each with a predetermined shape. The storage medium contains a program readable by a digital computer which instructs the digital computer to recognize the predetermined shape of each of the at-least-one portion as at least a part of a real-world fiducial in image data of a patient when the image data includes the predetermined shape and is received as an input by the digital computer. The position sensor is adapted to provide position data.

Several benefits and advantages are obtained from one or more of the embodiments of the invention. In one example of the first and/or second embodiment, image data is related to the fiducial component, the fiducial component is related to the position of the position sensor, and the position of the position sensor is related to a reference coordinate system allowing the creation of an image representation of the image data registered to the reference coordinate system and a display of an image of the image representation. In one variation, the fiducial component is attachable to the skin surface of the patient, the image data is obtained, and the fiducial component is removed and reattached to the same skin surface days later after which the image representation is created when the position of the attached/disposed sensor is indexed to the reference coordinate system and an image of the image representation is displayed and used while medically treating the patient. In one medical treatment, a medical instrument has its own position sensor, and an image of at least a part of the medical instrument is created and displayed superimposed on the image of the patient. An example of the third embodiment can be similarly employed.

DETAILED DESCRIPTION

Before explaining the several embodiments of the present invention in detail, it should be noted that the present invention is not limited in its application or use to the details of construction and arrangement of parts and steps illustrated in the accompanying drawings and description. The illustrative embodiments of the invention may be implemented or incorporated in other embodiments, methods, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described implementations, examples etc. can be combined with any one or more of the other following-described implementations, examples etc.

Figure 1:
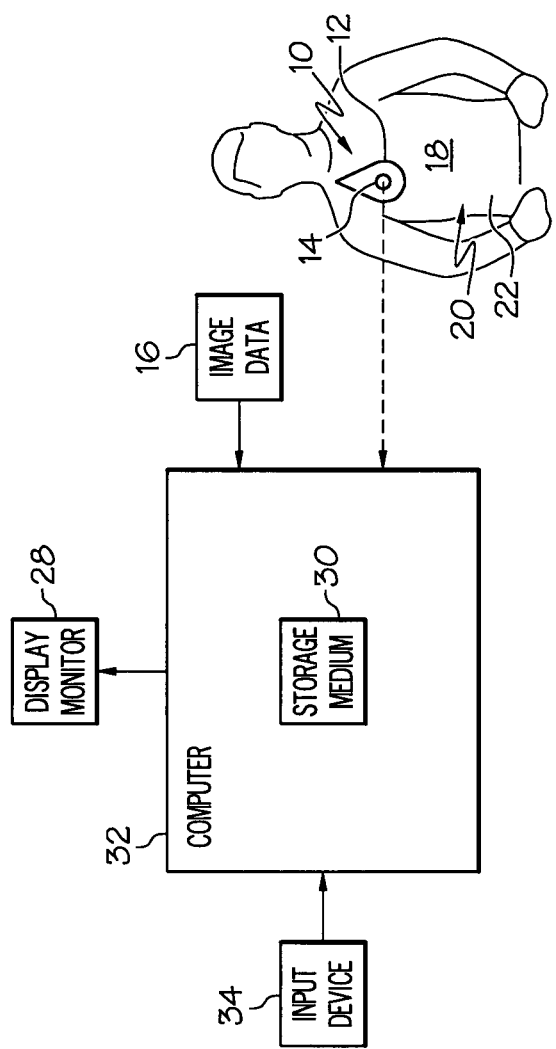
FIG. 1 is a schematic view of a first embodiment of the invention showing medical apparatus including a top planar view of a fiducial component and a position sensor (both shown in large scale), wherein the fiducial component is attached to a patient, and the position sensor is attached to the fiducial component.
Figure 2:
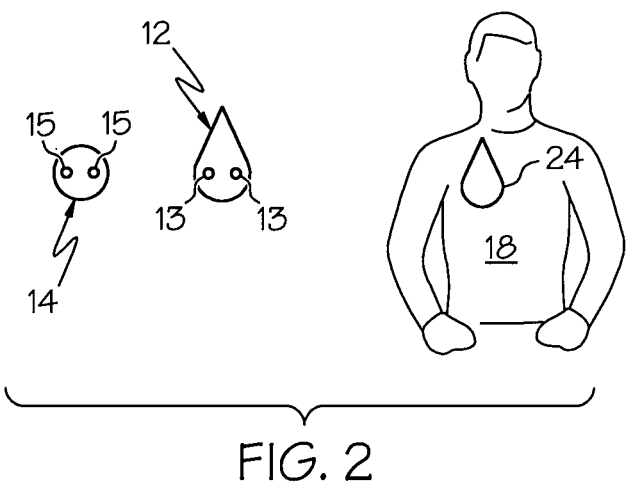
FIG. 2 is a schematic view a portion of FIG. 1 showing a top planar view of the location indicator on the patient, showing a top planar view of the fiducial component with its pin holes, and showing a bottom planar view of the position sensor with its pins, wherein the position sensor is not yet attached to the fiducial component and the fiducial component is not yet attached to the patient.
Figure 3:
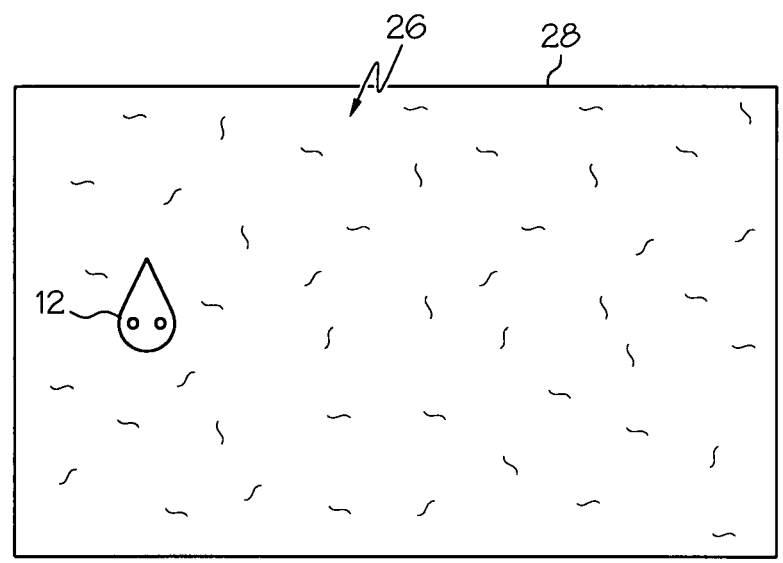
FIG. 3 is a schematic view of a display monitor upon which a digital computer displays an image of an image representation of image data of the patient registered to a reference coordinate system, wherein the fiducial component of FIG. 1 is shown in the image.

A first embodiment of the invention is shown in FIGS. 1-3. A first expression of the embodiment of FIGS. 1-3 is for medical apparatus 10 including a fiducial component 12 and a position sensor 14. The fiducial component 12 is recognizable as at least a part of a fiducial when appearing in image data 16 of a patient 18. The fiducial component 12 is attachable to the patient 18. The position sensor 14 is adapted to provide position data. The position sensor 14 is attachable to the fiducial component 12 at a predetermined location on the fiducial component 12 and with a predetermined orientation with respect to the fiducial component 12. It is noted that the fiducial component 12 has a predetermined shape which is recognizable as a "manufactured" shape as opposed to biological shapes occurring in image data of a patient. It is also noted that the position sensor 14 may be a wired or wireless sensor.

Examples of position sensors 14 adapted to provide position data include, without limitation, the position sensors of the AC-based position sensing system available from Biosense-Webster and the DC-based position sensing system available from Ascension Technology Corporation. It is noted that, as used in describing the embodiment of FIGS. 1-3, the term "position" includes up to six degrees of freedom so that calculating position includes calculating a two-dimensional or three-dimensional location (translation) and two or three degrees of orientation (alignment) of the sensor 14 with respect to a reference coordinate system. A description of the operation of an embodiment of a position sensor 14 adapted to provide position data is found in US Patent Application Publication 2006/0089624.

Examples of image data 16 include, without limitation, ultrasound image data, X-ray image data, computerized tomography (CT) image data, positive electron emission (PET) image data, magnetic resonance (MRI) image data, and fluoroscope image data. An example of a computer program which creates a manipulative 3D display image from 2D CT-scans and MRI-scans is Mimics available from Materialise of Ann Arbor, Mich.

In one enablement of the embodiment of FIGS. 1-3, the position sensor 14 is attached to the fiducial component 12. In one variation, the attachment is a temporary attachment meaning that the position sensor 14 can be detached from the fiducial component 12 without damage to either or both of the position sensor 14 and the fiducial component 12. In another variation, the attachment is a permanent attachment meaning that the position sensor 14 cannot be detached from the fiducial component 12 without damage to either or both of the position sensor 14 and the fiducial component 12.

In one implementation of the embodiment of FIGS. 1-3, the fiducial component 12 is recognizable as the fiducial. In one variation a portion of the overall shape of the fiducial component 12 is recognizable as the fiducial. In another variation, the overall shape of the fiducial component 12 is recognizable as the fiducial. In another implementation, it is the presence together of the fiducial component 12 (or a portion or portions thereof) and the position sensor 14 (or a portion or portions thereof) which is recognizable as the fiducial. In either or both implementations, separate portions may be recognized as separate fiducials.

In a first arrangement of the embodiment of FIGS. 1-3, the patient 18 has skin 20, wherein the skin 20 has a skin surface 22, wherein the fiducial component 12 is attachable to the skin surface 22 without piercing the skin surface 22, and wherein the position sensor 14 is attachable to the fiducial component 12 without piercing the skin surface 22. In one variation, the fiducial component 12 is adhesively attached to the skin surface 22. In the same or a different variation, the position sensor 14 has pins 15, the fiducial component 12 has pin holes 13, and the pins 15 are attachingly engagable with the pin holes 13. In one modification, not shown, the position sensor has a sensor body and a sensor, wherein the sensor body has a sensor location and rotational orientation feature such that the sensor is attachable to the sensor body only at the sensor location and with the rotational orientation. Other attachment variations and other modifications are left to the artisan.

A first method of the invention is for using the first arrangement of the medical apparatus 10 and includes steps a) through g). Step a) includes placing a location indicator 24 on the skin surface 22 where the fiducial component 12 is to be attached to the skin surface 22, wherein the location indicator 24 also indicates a desired orientation of the fiducial component 12 on the skin surface 22. Step b) includes, after step a), attaching the fiducial component 12 to the skin surface 22 at the location indicator 24 and with the desired orientation. Step c) includes, after step b), obtaining image data 16 of the patient 18, wherein the fiducial component 12 appears in the image data 16. Step d) includes, after step c), removing the fiducial component 12 from the skin surface 22 while leaving the location indicator 24 on the skin surface 22. Step e) includes, at a later time after steps a) through d), re-attaching the fiducial component 12 to the skin surface 22 at the location indicator 24 and with the desired orientation. Step f) includes, after step e), creating an image representation of the image data 16 indexed to a reference coordinate system using at least the recognized predetermined shape and a position of the position sensor 14 indexed to the reference coordinate system when the position sensor 14 is attached to the re-attached fiducial component 12. Step g) includes, after step f), displaying an image 26 of the image representation. It is noted that step c) may be performed with or without the position sensor 14 attached to the fiducial component 12.

In one realization of the first method, the position data and/or the image data 16 are already indexed and step e) does not perform such indexing. In a different realization of the first method, the position data and/or the image data 16 are not yet indexed, and step e) performs such indexing.

In one illustration of the first method, the position sensor 14 is considered to be a position sensor of a Biosense Webster positioning sensing system and a transmitter, not shown, of such system is used by a digital computer for a reference coordinate system for position data from the position sensor 14. Thus, the position of the position sensor 14 can be indexed to the reference coordinate system. Since the image data 16 is related to the fiducial component 12 which has a predetermined position with respect to the attached position sensor 14, an image representation of the image 26 can be created which is registered to the reference coordinate system.

In one employment of the first method, step g) displays the image 26 on a display monitor 28. Examples of a display monitor 42 include, without limitation, a computer monitor, a goggle display screen, and a room wall upon which projected images are displayed. In one variation, a storage medium 30 contains a program readable by a digital computer 32 which instructs the digital computer 32 to perform steps f) and g) of the first method.

In one example, the image 26 is a three-dimensional manipulative image, and there is also included a computer input device 34 operatively connected to the digital computer 32 to allow a user to manipulate the three-dimensional-manipulative image on the display monitor 28. Examples of input devices 34 include, without limitation, a keyboard and a mouse. In a different example, the image is a two-dimensional non-manipulative image.

In one variation of the first method, step e) is performed at least 24 hours after performing steps a) through d). In the same or a different variation, the location indicator 24 is an invisible ink outline of the fiducial component 12 on the skin surface 22 (such as the ultraviolet-ink outline made visible under ultraviolet light as seen in FIG. 2) or is a clear adhesive decal outline of the fiducial component on the skin surface. In one modification, the outline is asymmetric and matches the asymmetric shape of the fiducial component 12 for proper location and alignment of the fiducial component 12 on the skin surface 22. In the same or a different variation, the first method also includes the step of performing a medical treatment (such as a surgical treatment) of the patient 18 while viewing the displayed image 26. In one medical treatment, not shown, a medical instrument has its own position sensor, and an image of at least a part of the medical instrument is created and displayed superimposed on the image 26 of the patient 18. Other variations and modifications are left to the artisan including performing step e) at least 15 minutes after performing steps a) through d) or performing step e) at a shorter or longer time interval after performing steps a) through d). In one example, without limitation, a person who has had MRI or CT images taken in an imaging area of a medical facility where steps a) through d) were performed is then quickly moved to a surgical area of the medical facility where steps e) through g) are performed.

In a second arrangement of the embodiment of FIGS. 1-3, not shown, the fiducial component is attachable to an internal skeletal feature of the patient. In a third arrangement, not shown, the fiducial component is attachable to the patient below the skin of the patient, and the position sensor has at least one portion adapted for piercing the skin for attaching to the fiducial component. In a fourth arrangement, the fiducial component is attachable to the patient within the skin of the patient, and the position sensor has at least one portion adapted for piercing the skin surface for attaching to the fiducial component. In a fifth arrangement, the fiducial component is attachable to orthopedic hardware of the patient.

Figure 4:
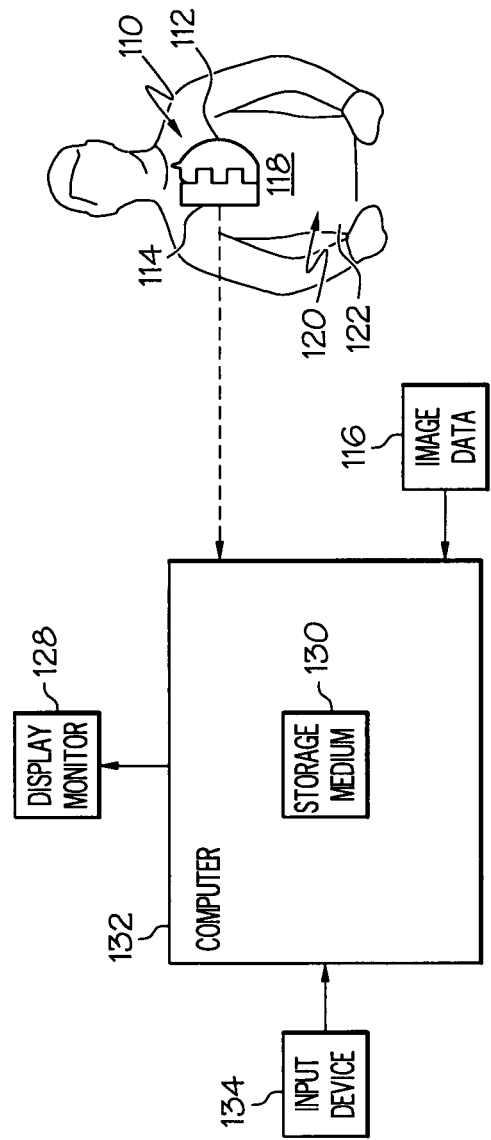
FIG. 4 is a schematic view of a second embodiment of the invention showing medical apparatus including a top planar view of a fiducial component and a position sensor (both shown in large scale), wherein the fiducial component is attached to a patient, and the position sensor is disposed adjacent the fiducial component without attachment thereto.
Figure 5:
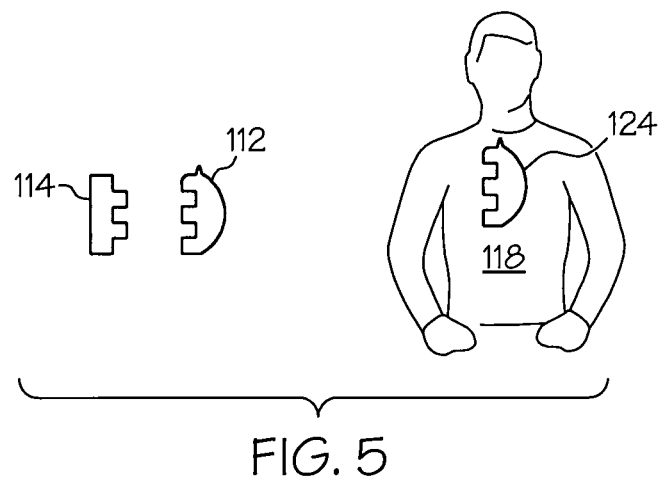
FIG. 5 is a schematic view of a portion of FIG. 3 showing a top planar view of the location indicator on the patient, showing a top planar view of the fiducial component, and showing a top planar view of the position sensor, wherein the position sensor is not yet disposed adjacent the fiducial component and the fiducial component is not yet attached to the patient.
Figure 6:
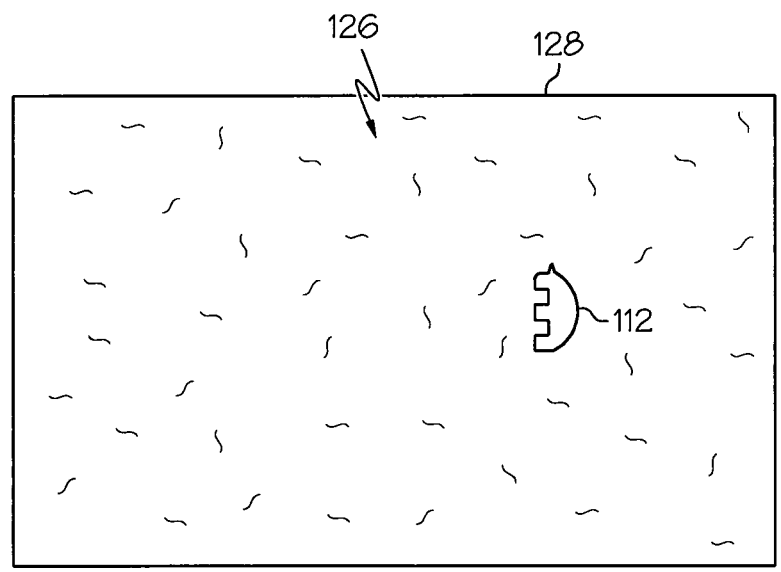
FIG. 6 is a schematic view of a display monitor upon which a digital computer displays an image of an image representation of image data of the patient registered to a reference coordinate system, wherein the fiducial component of FIG. 4 is shown in the image.

A second embodiment of the invention is shown in FIGS. 4-6. A first expression of the embodiment of FIGS. 4-6 is for a medical apparatus 110 including a fiducial component 112 and a position sensor 114. The fiducial component 112 is recognizable as at least a part of a fiducial when appearing in image data 116 of a patient 118. The fiducial component 112 is attachable to the patient 118. The position sensor 14 is adapted to provide position data. The position sensor 114 is disposable adjacent the fiducial component 112 without attachment thereto at a predetermined location on the fiducial component 112 and with a predetermined orientation with respect to the fiducial component 112. It is noted that the fiducial component 112 has a predetermined shape which is recognizable as a "manufactured" shape as opposed to biological shapes occurring in image data of a patient.

In one enablement of the embodiment of FIGS. 4-6, the position sensor 114 is disposed adjacent the fiducial component 112 without attachment thereto at the predetermined location on the fiducial component 112 and with the predetermined orientation with respect to the fiducial component 112.

In one implementation of the embodiment of FIGS. 4-6, the fiducial component 112 is recognizable as the fiducial.

In a first arrangement of the embodiment of FIGS. 4-6, the patient 118 has skin 120, wherein the skin 120 has a skin surface 122, wherein the fiducial component 112 is attachable to the skin surface 122 without piercing the skin surface 122, and wherein the position sensor 114 is attachable to the skin surface 122 adjacent the fiducial component 112 without piercing the skin surface 122. In one variation, the fiducial component 112 and the position sensor 114 each are adhesively attached to the skin surface 122. In the same or a different variation, the position sensor 114 and the fiducial component 112 each have a complementary-shaped portion which allows the position sensor 114 to be disposed adjacent the fiducial component 112 at a desired location on the fiducial component 112 and with a desired alignment with respect to the fiducial component 112.

A second method of the invention is for using the first arrangement of the medical apparatus 110 and includes steps a) through g). Step a) includes placing a location indicator 124 on the skin surface 122 where the fiducial component 112 is to be attached to the skin surface 122, wherein the location indicator 124 also indicates a desired orientation of the fiducial component 112 on the skin surface 122. Step b) includes, after step a), attaching the fiducial component 112 to the skin surface 122 at the location indicator 124 and with the desired orientation. Step c) includes, after step b), obtaining image data 116 of the patient 118, wherein the fiducial component 112 appears in the image data 116. Step d) includes, after step c), removing the fiducial component 112 from the skin surface 122 while leaving the location indicator 124 on the skin surface 122. Step e) includes, at a later time after steps a) through d), re-attaching the fiducial component 112 to the skin surface 122 at the location indicator 124 and with the desired orientation. Step f) includes, after step e), creating an image representation of the image data 116 indexed to a reference coordinate system using at least the recognized predetermined shape and a position of the position sensor 114 indexed to the reference coordinate system when the position sensor 114 is disposed adjacent the re-attached fiducial component 112. Step g) includes, after step f), displaying an image 126 of the image representation. It is noted that step c) may be performed with or without the position sensor 114 disposed adjacent (e.g., on the side or top surface of) the re-attached fiducial component 112 at the desired location on the fiducial component 112 and with the desired alignment with respect to the fiducial component 112.

In one illustration of the second method, the position sensor 114 is considered to be a position sensor of a Biosense Webster positioning sensing system and a transmitter, not shown, of such system is used by a digital computer for a reference coordinate system for position data from the position sensor 114. Thus, the position of the position sensor 114 can be indexed to the reference coordinate system. Since the image data 116 is related to the fiducial component 112 which has a predetermined position with respect to the properly adjacently disposed position sensor 114, an image representation of the image 126, can be created which is registered to the reference coordinate system.

In one employment of the second method, step g) displays the image 126 on a display monitor 128. In one variation, a storage medium 130 contains a program readable by a digital computer 132 which instructs the digital computer 132 to perform steps f) and g) of the second method.

In one example, the image 126 is a three-dimensional manipulative image, and there is also included a computer input device 134 operatively connected to the digital computer 132 to allow a user to manipulate the three-dimensional-manipulative image on the display monitor 128. In a different example, the image is a two-dimensional non-manipulative image.

In one variation of the second method, step e) is performed at least 24 hours after performing steps a) through d). In the same or a different variation, the location indicator 124 is an invisible ink outline of the fiducial component 112 on the skin surface 122 (such as the ultraviolet-ink outline made visible under ultraviolet light as seen in FIG. 5) or is a clear adhesive decal outline of the fiducial component on the skin surface. In one modification, the outline is asymmetric and matches the asymmetric shape of the fiducial component 112 for proper location and alignment of the fiducial component 112 on the skin surface 122. In the same or a different variation, the second method also includes the step of performing a medical treatment (such as a surgical treatment) of the patient 118 while viewing the displayed image 126. In one medical treatment, not shown, a medical instrument has its own position sensor, and an image of at least a part of the medical instrument is created and displayed superimposed on the image 126 of the patient 118.

Figure 7:
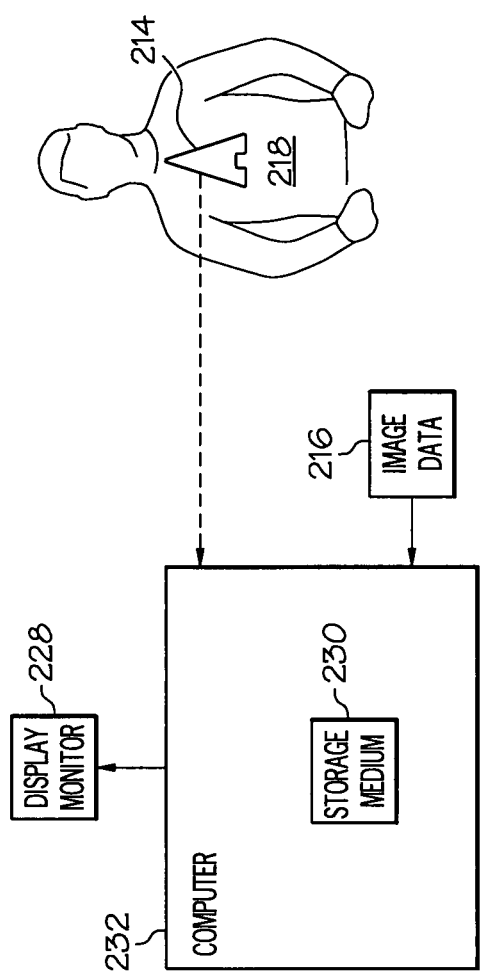
FIG. 7 is a schematic view of a third embodiment of the invention showing medical apparatus including a top planar view of a position sensor, wherein the position sensor is attached to a patient.
Figure 8:
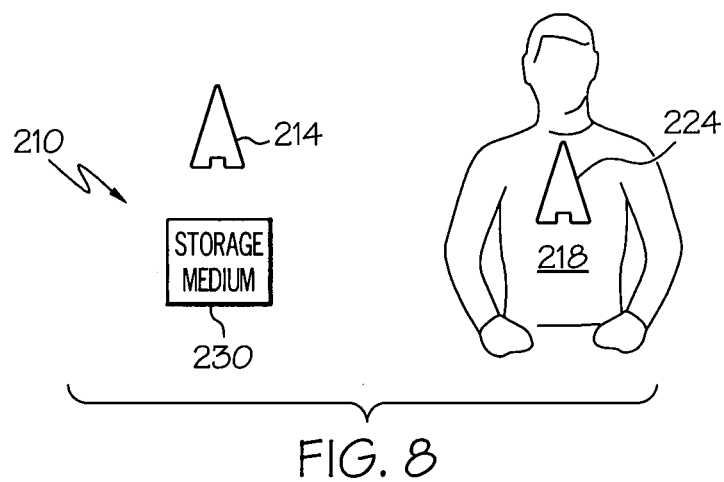
FIG. 8 is a schematic view a portion of FIG. 7 showing a top planar view of the location indicator on the patient and showing a top planar view of the position sensor, wherein the position sensor is not yet attached to the patient.
Figure 9:
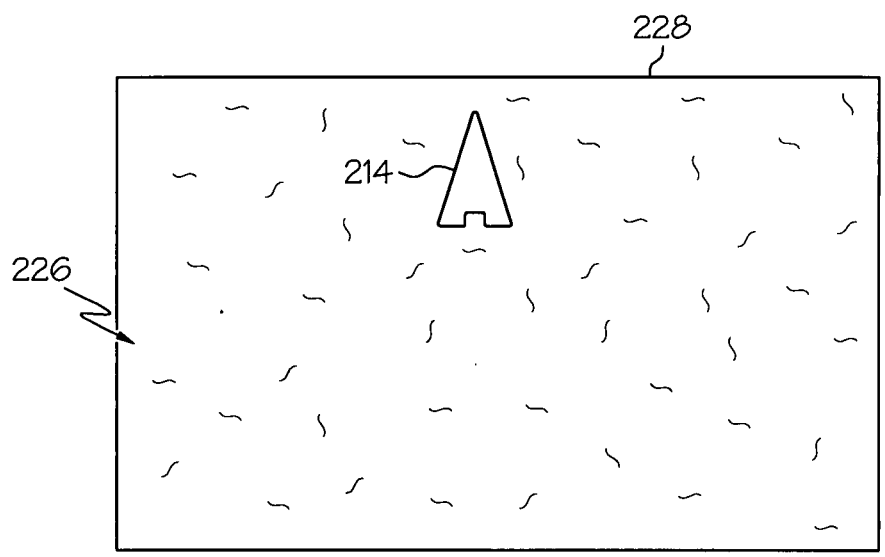
FIG. 9 is a schematic view of a display monitor upon which a digital computer displays an image of an image representation of image data of the patient registered to a reference coordinate system, wherein the position sensor of FIG. 7 is shown in the image.

A third embodiment of the invention is shown in FIGS. 7-9. A first expression of the embodiment of FIGS. 7-8 is for a storage medium 230 containing a program readable by a digital computer 232 which instructs the digital computer 232 to recognize a predetermined shape of each of at least one portion of a position sensor 214 as at least a part of a real-world fiducial in image data 216 of a patient 218 when the image data 216 includes the predetermined shape and is received as an input by the digital computer 232. The position sensor 214 is adapted to provide position data. It is noted that the words "at least one portion" includes "the entirety". In one example, the program includes a conventional segmentation subroutine to identify the predetermined shape.

Examples of storage media include, without limitation, temporary computer memory and permanent computer memory such as RAM, hard drives, CD's, etc.

In one enablement of the first expression of the embodiment of FIGS. 7-9, the at-least-one portion is adapted to have a fixed position relative to the patient 218 during a medical treatment of the patient 218. In the same or a different enablement, the program instructs the digital computer 232 to create an image representation of the image data 216 indexed to a reference coordinate system using at least the recognized predetermined shape and a position of the position sensor indexed to the reference coordinate system, and the program instructs the digital computer 232 to display an image 226 (such as on a display monitor 228) of the image representation. It is noted that code can be written by those of ordinary skill in the art, without undue experimentation, which instructs the digital computer 132 to create the image representation of the image data 116 indexed to the reference coordinate system.

In one extension of the first expression of the embodiment of FIGS. 7-9, a location indicator 224 (similar to the previously described location indicators 24 and 124) is disposed on the patient 218, and the position sensor 214 is disposable on the patient 218 on, and alignable with, the location indicator 224.

A second expression of the embodiment of FIGS. 7-9 is for medical apparatus 210 including a position sensor 214 and a storage medium 230. The position sensor 214 has at least one portion each with a predetermined shape. The storage medium 230 contains a program readable by a digital computer 232 which instructs the digital computer 232 to recognize the predetermined shape of each of the at-least-one portion as at least a part of a real-world fiducial in image data 216 of a patient 218 when the image data 216 includes the predetermined shape and is received as an input by the digital computer 232. The position sensor 214 is adapted to provide position data.

It is noted that the enablements, etc. of the first expression of the embodiment of FIGS. 7-9 are equally applicable to the second expression of the embodiment of FIGS. 7-9.

Several benefits and advantages are obtained from one or more of the embodiments of the invention. In one example of the first and/or second embodiment, image data is related to the fiducial component, the fiducial component is related to the position of the position sensor, and the position of the position sensor is related to a reference coordinate system allowing the creation of an image representation of the image data registered to the reference coordinate system and a display of an image of the image representation. In one variation, the fiducial component is attachable to the skin surface of the patient, the image data is obtained, and the fiducial component is removed and reattached to the same skin surface days later after which the image representation is created when the position of the attached/disposed sensor is indexed to the reference coordinate system and an image of the image representation is displayed and used while medically treating the patient. In one medical treatment, a medical instrument has its own position sensor, and an image of at least a part of the medical instrument is created and displayed superimposed on the image of the patient. An example of the third embodiment can be similarly employed.

While the present invention has been illustrated by several embodiments and methods, and enablements, applications, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A medical apparatus comprising a location indicator, a fiducial component, and a position sensor, wherein the location indicator is disposable upon a patient skin surface and uniquely indicates a desired orientation of the fiducial component on the skin surface, wherein the fiducial component is recognizable as at least a part of a fiducial when appearing in image data of a patient, wherein the fiducial component is attachable to the patient at the location indicator without piercing the skin surface and is non-destructively separable from the location indicator, wherein the position sensor is attachable to the patient without piercing the skin surface and adapted to provide position data, wherein the position sensor is adjoinable to the fiducial component without attachment thereto at a predetermined location on the fiducial component and with a predetermined orientation with respect to the fiducial component, and wherein the fiducial component and the position sensor each have a complementary-shaped abutment portion such that mutual abutment without mutual attachment disposes the position sensor at the predetermined location on the fiducial component and with the predetermined orientation with respect to the fiducial component.

2. A method for using a medical apparatus that comprises a location indicator, a fiducial component, and a position sensor, wherein the location indicator is disposable upon a patient skin surface and uniquely indicates a desired orientation of the fiducial component on the skin surface, wherein the fiducial component is recognizable as at least a part of a fiducial when appearing in image data of a patient, wherein the fiducial component is attachable to the patient at the location indicator and is non-destructively separable from the location indicator, wherein the position sensor is adapted to provide position data, wherein the position sensor is adjoinable to the fiducial component without attachment thereto at a predetermined location on the fiducial component and with a predetermined orientation with respect to the fiducial component, wherein the fiducial component is attachable to the patient at the location indicator without piercing the skin surface, wherein the position sensor is attachable to the patient without piercing the skin surface, and wherein the position sensor and the fiducial component each have a complementary-shaped abutment portion such that mutual abutment without mutual attachment disposes the position sensor at the predetermined location on the fiducial component and with the predetermined orientation with respect to the fiducial component, the method comprising the steps of:
 a) placing the location indicator on the skin surface where the fiducial component is to be attached to the skin surface and so as to indicate the desired orientation of the fiducial component on the skin surface;
 b) after step a), attaching the fiducial component to the skin surface at the location indicator and with the indicated orientation;
 c) after step b), obtaining image data of the patient, wherein the fiducial component appears in the image data;
 d) after step c), removing the fiducial component from the skin surface while leaving the location indicator on the skin surface; and
 e) at a later time after steps a) through d), re-attaching the fiducial component to the skin surface at the location indicator and with the indicated orientation;
 f) after step e), placing the position sensor on the skin surface, in adjoinment with the fiducial component without attachment thereto at the predetermined location on the fiducial component and with the predetermined orientation with respect to the fiducial component, wherein said adjoinment includes abutting the complementary-shaped abutment portion of the position sensor against the complementary-shaped abutment portion of the fiducial component, and creating an image representation of the image data indexed to a reference coordinate system using at least the recognized predetermined shape and a position of the position sensor indexed to the reference coordinate system when the position sensor is in adjoinment with the re-attached fiducial component; and
 g) after step f), displaying an image of the image representation.

3. The method of claim 2, wherein step e) is performed at least 24 hours after performing steps a) through d).

4. The method of claim 3, wherein the location indicator is an invisible ink outline of the fiducial component disposed on the skin surface.

5. A medical apparatus comprising a location indicator, a fiducial component, and a position sensor, wherein the location indicator is disposable upon a patient skin surface to present an outline of the fiducial component, wherein the fiducial component has a rotationally asymmetric shape and is recognizable as at least a part of a fiducial when appearing in image data of the patient, wherein the fiducial component is attachable to the patient over or within the location indicator without piercing the skin surface and is non-destructively separable from the location indicator, wherein the position sensor is adapted to provide position data, wherein the position sensor is attachable to the skin surface adjacent the fiducial component without piercing the skin surface and adjoinable to the fiducial component without attachment thereto at a predetermined location on the fiducial component and with a predetermined orientation with respect to the fiducial component, and wherein the fiducial component and the position sensor each have a complementary-shaped abutment portion such that mutual abutment without mutual attachment disposes the position sensor at the predetermined location on the fiducial component and with the predetermined orientation with respect to the fiducial component.

6. A method for using a medical apparatus that comprises a location indicator, a fiducial component, and a position sensor, wherein the location indicator is disposable upon a patient skin surface to present an outline of the fiducial component, wherein the fiducial component has a rotationally asymmetric shape and is recognizable as at least a part of a fiducial when appearing in image data of the patient, wherein the fiducial component is attachable to the patient over or within the location indicator and is non-destructively separable from the location indicator, wherein the position sensor is adapted to provide position data, wherein the position sensor is adjoinable to the fiducial component without attachment thereto at a predetermined location on the fiducial component and with a predetermined orientation with respect to the fiducial component, wherein the fiducial component is attachable to the patient over or within the location indicator without piercing the skin surface, wherein the position sensor is attachable to the skin surface adjacent the fiducial component without piercing the skin surface, and wherein the fiducial component and the position sensor each have a complementary-shaped abutment portion such that mutual abutment without mutual attachment disposes the position sensor at the predetermined location on the fiducial component and with the predetermined orientation with respect to the fiducial component, the method comprising the steps of:

a) placing the location indicator on the skin surface where the fiducial component is to be attached to the skin surface, wherein the location indicator is an outline, having a rotationally asymmetric shape matching the rotationally asymmetric shape of the fiducial component, that indicates a desired orientation of the fiducial component on the skin surface;

b) after step a), attaching the fiducial component to the skin surface at the location indicator and with the indicated orientation;

c) after step b), obtaining image data of the patient, wherein the fiducial component appears in the image data;

d) after step c), removing the fiducial component from the skin surface while leaving the location indicator on the skin surface; and e) at a later time after steps a) through d), re-attaching the fiducial component to the skin surface at the location indicator and with the indicated orientation;

f) after step e), placing the position sensor on the skin surface, in adjoinment with the fiducial component without attachment thereto at the predetermined location on the fiducial component and with the predetermined orientation with respect to the fiducial component, wherein said adjoinment includes abutting the complementary-shaped abutment portion of the position sensor against the complementary-shaped abutment portion of the fiducial component, and creating an image representation of the image data indexed to a reference coordinate system using at least the recognized predetermined shape and a position of the position sensor indexed to the reference coordinate system when the position sensor is disposed in adjoinment with the re-attached fiducial component; and g) after step f), displaying an image of the image representation.

7. The method of claim 6, wherein step e) is performed at least 24 hours after performing steps a) through d).

8. The method of claim 7, wherein the location indicator is an invisible ink outline of the fiducial component disposed on the skin surface.

9. The method of claim 3, wherein the location indicator is a clear adhesive decal outline of the fiducial component disposed on the skin surface.

10. The method of claim 3, wherein the placing of the location indicator includes placing an outline of the fiducial component on the patient skin surface in an invisible ink.

11. The method of claim 7, wherein the location indicator is a clear adhesive decal outline of the fiducial component disposed on the skin surface.

12. The method of claim 7, wherein the placing of the location indicator includes placing an outline of the fiducial component on the patient skin surface in an invisible ink.

13. The medical apparatus of claim 1, wherein the complementary-shaped abutment portions are outermost peripheral surfaces of the respective fiducial component and position sensor.

14. The method of claim 2, wherein the complementary-shaped abutment portions are outermost peripheral surfaces of the respective fiducial component and position sensor.

15. The medical apparatus of claim 5, wherein the complementary-shaped abutment portions are outermost peripheral surfaces of the respective fiducial component and position sensor.

16. The method of claim 6, wherein the complementary-shaped abutment portions are outermost peripheral surfaces of the respective fiducial component and position sensor.

* * * * *